(12) United States Patent
Olson

(10) Patent No.: US 11,504,141 B2
(45) Date of Patent: Nov. 22, 2022

(54) INSERTABLE MEDICAL DEVICE SYSTEM WITH PLAQUE TREATMENT PORTION AND METHODS OF USING

(71) Applicant: Surmodics, Inc., Eden Prairie, MN (US)

(72) Inventor: Charlie Olson, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 374 days.

(21) Appl. No.: 16/687,256

(22) Filed: Nov. 18, 2019

(65) Prior Publication Data

US 2020/0155179 A1 May 21, 2020

Related U.S. Application Data

(62) Division of application No. 15/053,526, filed on Feb. 25, 2016, now Pat. No. 10,524,809.

(60) Provisional application No. 62/121,349, filed on Feb. 26, 2015.

(51) Int. Cl.
| | |
|---|---|
| *A61B 17/22* | (2006.01) |
| *A61B 17/3207* | (2006.01) |
| *A61M 25/10* | (2013.01) |
| *A61B 17/32* | (2006.01) |
| *A61B 17/00* | (2006.01) |

(52) U.S. Cl.
CPC ...... *A61B 17/22* (2013.01); *A61B 17/320725* (2013.01); *A61M 25/104* (2013.01); *A61B 2017/00685* (2013.01); *A61B 2017/22001* (2013.01); *A61B 2017/22051* (2013.01); *A61B 2017/22061* (2013.01); *A61B 2017/22084* (2013.01); *A61B 2017/320004* (2013.01); *A61B 2017/320008* (2013.01); *A61M 2025/105* (2013.01); *A61M 2025/109* (2013.01); *A61M 2025/1086* (2013.01)

(58) Field of Classification Search
CPC .......... A61B 17/22; A61M 2025/0175; A61M 2025/0681; A61M 2025/0039; A61M 2025/1086; A61M 2025/1088; A61M 2025/109; A61M 25/1006; A61F 2/958; A61F 2/962

See application file for complete search history.

(56) References Cited

U.S. PATENT DOCUMENTS

| | | | |
|---|---|---|---|
| 10,286,186 | B2 | 5/2019 | Okamura |
| 2002/0151924 | A1 | 10/2002 | Shiber |
| 2002/0156496 | A1 | 10/2002 | Chermoni |
| 2004/0143287 | A1 | 7/2004 | Konstantino et al. |
| 2006/0259005 | A1 | 11/2006 | Konstantino et al. |

(Continued)

*Primary Examiner* — Dung T Ulsh
(74) *Attorney, Agent, or Firm* — Kagan Binder, PLLC

(57) ABSTRACT

The disclosure provides plaque treatment catheter assemblies for the treatment of arterial plaques and removal of clots. One assembly includes a second catheter tube movable within a first catheter tube, and an expansion member movable within the second tube. The second catheter tube has one or more distally-disposed and outwardly-expandable plaque treatment portion(s). Another assembly includes a catheter tube and at least one channel(s) within the catheter. The channel includes an elongate member with a distally-disposed plaque scoring or clot retrieval member. Optionally, the assembly includes an expandable member that can cause movement of the scoring member.

9 Claims, 10 Drawing Sheets

(56) References Cited

U.S. PATENT DOCUMENTS

| | | |
|---|---|---|
| 2009/0105686 A1 | 4/2009 | Snow |
| 2010/0331816 A1 | 12/2010 | Dadino et al. |
| 2011/0040319 A1 | 2/2011 | Fulton, III |
| 2012/0035705 A1 | 2/2012 | Giasolli et al. |
| 2013/0096604 A1 | 4/2013 | Hanson et al. |
| 2013/0144263 A1 | 6/2013 | Eyal et al. |
| 2013/0150874 A1 | 6/2013 | Kassab |
| 2013/0226071 A1 | 8/2013 | Konstantino et al. |
| 2013/0261547 A1 | 10/2013 | Aggerholm et al. |
| 2014/0107481 A1 | 4/2014 | Wulfman |
| 2014/0142598 A1* | 5/2014 | Fulton, III ..... A61B 17/320725 606/159 |
| 2014/0324079 A1 | 10/2014 | Silvestro |
| 2016/0249942 A1 | 9/2016 | Olson |
| 2017/0196476 A1 | 7/2017 | Kassab |
| 2017/0209160 A1 | 7/2017 | Pigott |
| 2017/0224363 A1 | 8/2017 | Watanabe et al. |

\* cited by examiner

INSERTABLE MEDICAL DEVICE SYSTEM WITH PLAQUE TREATMENT PORTION AND METHODS OF USING

CROSS-REFERENCE TO RELATED APPLICATION

The present application is a divisional of U.S. application Ser. No. 15/053,526, filed Feb. 25, 2016, which claims the benefit of Provisional Application No. 62/121,349, filed Feb. 26, 2015, entitled INSERTABLE MEDICAL DEVICE SYSTEM WITH PLAQUE TREATMENT PORTION AND METHODS OF USING, wherein the entirety of said patent applications are incorporated herein by reference.

FIELD

The current inventions relates to catheter systems for the treatment of arterial plaques, and methods for using the plaque treatment system.

BACKGROUND

Atherosclerosis is a disease that affects arteries of the body, with most cases affecting the coronary arteries. During the onset of atherosclerosis, changes in the walls of the arteries are seen characterized by increases in cholesterol content and scar tissue. Later on, atherosclerotic plaques build up and thicken the wall of the artery, often causing arterial narrowing artery resulting in reduced blood flow. At these later stages, calcium can be present in the plaques.

As a general matter, it is desired to treat patients found to have plaques because, whether the plaque impedes blood flow or not, their presence presents a risk of rupture which could trigger a coronary event. A ruptured plaque can stimulates local formation of a blood clot that can block the flow of blood to the heart muscle and cause myocardial infarction.

SUMMARY

The present invention is directed to medical devices and systems, and also the use of such systems for treating arterial plaques. The system can be used for treating one or more arterial plaques using a mechanical scoring process, a drug delivery process, or combinations thereof. The system provides advantages over other known catheter systems of the art with regards to ease of use, versatility, and effectiveness.

In one embodiment, the invention provides a plaque treatment catheter assembly comprising a first catheter tube, a second catheter tube, and an expansion member. The first catheter tube has an inner and outer diameter and is capable of being inserted within the vasculature. The second catheter tube has an outer diameter that is smaller than the inner diameter of the first catheter tube and capable is of moving within and out of the first catheter tube. The second catheter tube also has a distal portion comprising one or more plaque treatment portion(s) on its outer surface. The plaque treatment portion(s) can include a scoring member that can abrade a plaque, a bioactive agent useful for treating the plaque, or a combination thereof. At the plaque treatment portion, the second catheter tube is capable of outward expansion in response to pressure of an expansion member on an inner surface of the second catheter tube. The expansion member, such as a balloon portion of a balloon catheter, is movable within and out of the inner diameter of the second catheter tube when the expansion member is in a contracted state.

In another embodiment, the invention provides a method for treating an arterial plaque, comprising a step of treating one or more arterial plaque(s) with the plaque treatment portion of the second catheter tube of the plaque treatment catheter assembly. For example, the treatment method can include expanding the expansion member which is forced against the inner wall of the second tube, and which causes the plaque treatment portion to press up against the plaque. If a scoring member is present, the plaque can effectively be abraded, or if a bioactive agent coating is present, bioactive agent can be released to the plaque. The expansion member can then be contracted, such as by deflation of a balloon. The second tube can be moved to a different treatment site, or withdrawn back into the first tube.

In another embodiment, the invention provides a plaque treatment catheter assembly that includes a catheter tube that has proximal and distal catheter ends, and an inner and outer diameter defining a catheter wall, the catheter tube capable of being inserted within the vasculature. There are one or more channel(s) within the catheter wall that are parallel to an axis of the catheter tube and that extend from the proximal to distal end of the catheter tube. The assembly also includes an elongate member having a distal portion comprising a plaque scoring member or a clot retrieval member, and a portion proximal to the distal portion configured to move within the channel. Optionally, the assembly includes an expandable member that is movable within and out of the inner diameter of the catheter tube that can be expanded to cause movement of the one or more scoring element(s).

The unique design of the system facilitates plaque treatment, particularly when there are multiple sites within in artery in need of treatment. Further, the current system can also minimize device movement in and out of the patient. For example, the current system allows a single pairing of the second tube (with plaque treatment portion) with the expandable member (e.g., balloon catheter), which can be used for plaque treatment, without having to introduce multiple devices within the artery. This in turn, can provide improved levels of patient safety.

DETAILED DESCRIPTION

Figure 1:
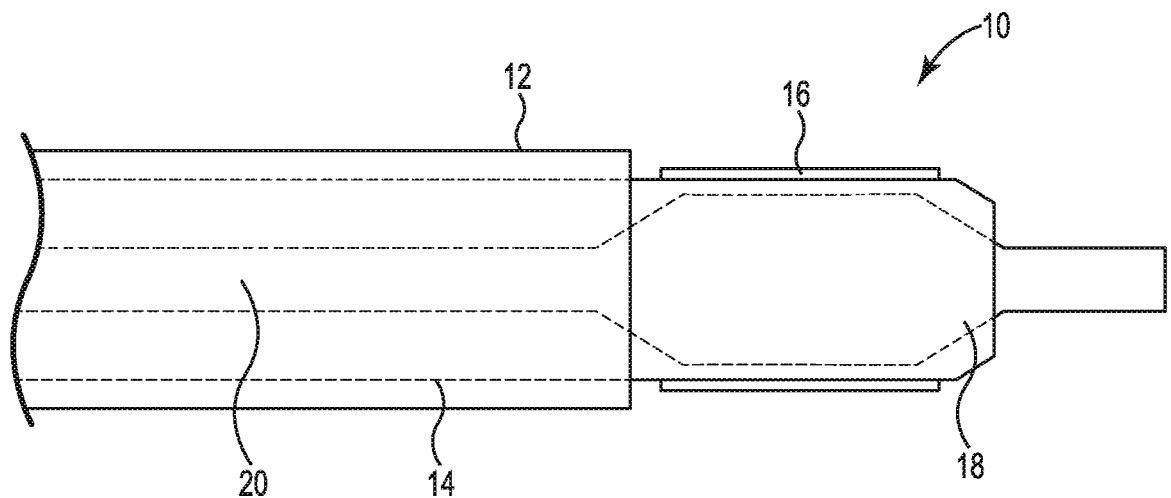
FIG. 1 is a cross-sectional side illustration a distal end of a plaque treatment system with first tube, second tube, and balloon catheter.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The terms "proximal" and "distal" are used herein to define the location of certain features of the catheter treatment system and method of using it. The proximal end ("user end") refers to location of a feature of the system that is towards the user, i.e., towards the outside the body. The distal end ("treatment end") refers to location of a feature of the system that is away from the user end, i.e., towards the treatment site. A "proximal portion" refers to a portion that is more towards the proximal end relative to a portion that is more towards the distal end, which is a "distal portion." The "inner surface" ("luminal surface") refers to the surface of an article that is within the lumen of a hollow article, whereas the "outer surface" refers to the surface on the outside of the hollow article ("abluminal surface"). Likewise, the inner surface of such an article can define an "inner diameter," and the outer surface can define an "outer diameter," wherein the difference between the outer and inner diameters can define a "wall thickness," such as the thickness of the wall of the second catheter tube. The inner and outer diameters, and wall thickness can also be defined for a hollow article such as second tube, when it is in an expanded state.

Generally, the disclosure provides medical devices and systems, and methods for treating arterial plaques. In one embodiment, the system includes a second catheter tube comprising one or more plaque treatment portion(s) that are used to treat an arterial plaque(s). The system also includes a first catheter tube, wherein the second catheter tube movable within the first catheter tube. The system also includes an expandable member, such as a balloon portion of a balloon catheter. The expandable member can be movable within the second catheter tube having the plaque treatment portion. For example, a balloon catheter can be movable within the second catheter tube.

In a method for treating arterial plaques, the plaque treatment portion of the second catheter tube is moved to an arterial treatment site (e.g., the site of an arterial plaque). In particular, the second catheter tube is moved so the plaque treatment portion, which includes a plaque-scoring member, a bioactive agent that can treat the plaque, or both, can contact the plaque. The balloon portion of the balloon catheter is placed within the second catheter tube inside the plaque treatment portion. The balloon portion of the balloon catheter is placed within the second catheter tube inside the plaque treatment portion. The balloon portion is then expanded within the second tube, exerting force against the inner diameter of the second tube and causing it to expand and press the plaque treatment portion up against the plaque. This action causes the plaque to be scored, bioactive agent release to the plaque, or both.

A cross-sectional side view of an exemplary construction is shown in FIG. 1. The distal end 10 of a plaque treatment system is shown, with first tube 12, second tube 14 with plaque treatment portion 16, and expandable member 18, which can be a balloon portion of a balloon catheter having balloon catheter tube 20.

The first tube can include proximal and distal ends, and can be configured to allow the second tube to travel within it. The first tube can be constructed from one or more materials that allow it to be moved in within the lumen of an artery. The outer surface of the first tube can be lubricious to facilitate its movement in the artery, and lubricity can be provided by a hydrophilic coating. The inner diameter of the tube can also have a coating to facilitate movement of the plaque treatment portion and can also protect the plaque treatment portion while it is moved within the first tube.

In some embodiments the first tube can be made of a material that is more rigid than any portion of the second tube (such as the plaque treatment portion of the second tube), but still flexible enough to be navigated through an artery. The first tube can be formed from any desirable material, or combination of materials, suitable for use within the body. Exemplary articles and materials that can be used as or to construct the first tube include, but are not limited to, metal hypotube, polymer shafts (e.g., made from polyamides, polyamide block copolymers, such as PEBAX of various durometers, polyetheretherketone (PEEK), high density polyethylene, polyimide, PTFE) with or without embedded longitudinal support wires, braids, or coiled shafts. In some embodiments the first tube is formed from compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The first tube can be made of a single elastomeric material, or a combination of materials. Other materials for the first tube can include those formed of addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Beyond polymers, and depending on the type of device, the first tube can also be formed of other inorganic materials such as metals (including metal foils and metal alloys), glass, or ceramics.

Processes to modify the first tube described above can include chemical modifications to improve performance characteristics of the first tube. Specific chemical processes that can be used include ozone treatment, chemical oxidation, acid chemical etching, base chemical etching, plasma treatment and corona treatment, surface grafting, thermally activated coating processes (both covalent and non-covalent) and surface modifications including coatings containing dopamine, tannic acid, plant polyphenols and other catechols or catechol-containing derivatives of hydrophilic moieties. Additionally, processes to form first tubes described above can include physical modifications such as sand blasting and surface texturing, which can be performed either during or after a polymeric molding process to form the tube.

In some embodiments, the modification of first tube as described herein can allow for omission of a base coating layer (such as a hydrophilic layer) as first tube surfaces that have been modified will allow for improved adhesion of a hydrophobic therapeutic agent and cationic agent compared with that of a hydrophilic layer.

Exemplary outer diameters for the first tube are in the range of about 1 mm (3 Fr) to 10 mm (30 Fr), about 1 mm (3 Fr) to about 3.3 mm (10 Fr), about 2 mm (6 Fr) to about 4 mm (12 Fr), about 2 mm (6 Fr) to about 8 mm (24 Fr), or about 3.3 mm (10 Fr) to about 4 mm (12 Fr). The inner diameter can be large enough to accommodate the plaque treatment portion when it is in an unexpanded state. Exemplary inner diameters for the first tube are in the range of about 0.5 (1.5 Fr) mm to about 9.33 mm (28 Fr), or about 1 mm (3 Fr) to about 8 mm (24 Fr). The wall thickness of the first tube can be in the range of about 35 μm to 500 or about 50 μm to 1 mm.

The first tube can also include one or more imaging material(s) to facilitate the location of one of more parts of the first tube during a medical procedure. The imaging materials can be applied to, or incorporated into, the first tube at one or more locations along its length. Exemplary imaging materials include paramagnetic material, such as nanoparticular iron oxide, Gd, or Mn, a radioisotope, and non-toxic radio-opaque markers (for example, cage barium sulfate and bismuth trioxide). Common radio opaque materials include barium sulfate, bismuth subcarbonate, and zirconium dioxide. Other radio opaque materials include cadmium, tungsten, gold, tantalum, bismuth, platinum, iridium, and rhodium. Paramagnetic resonance imaging, ultrasonic imaging, x-ray means, fluoroscopy, or other suitable detection techniques can be used to detect the imaging material.

Other exemplary imaging tools and techniques to facilitate location of one or more parts of the first tube can include intravascular imaging, for example, but not limited to, intravascular ultrasound and the like (e.g., from Volcano Corporation, San Diego, Calif.).

The second tube includes proximal and distal ends, with a plaque treatment portion including one or more plaque treatment members, the plaque treatment portion being located at a distal portion of the tube, which is towards the distal end. The second tube can be constructed from one or more materials that allow it to be moved in relation to the first tube. The materials of the second tube should also allow the expandable member, such as a balloon catheter tube, to move within the second tube. Further a portion of the second tube that include at least one or more plaque treatment portions is capable of being expanded in an outward direction in response to pressure exerted from the expandable member within the tube. In an expanded state, portion of second tube at the plaque treatment portion is able to press up against the arterial plaque to affect it, such as by physical abrasion of the plaque, delivery of a therapeutic agent to the plaque, or both.

Unlike a balloon of a balloon catheter, the second tube is not necessarily inflatable, but rather expandable at least at the plaque treatment portion(s).

The plaque delivery portion of the second tube is capable of being expanded in response to pressure from the balloon. Therefore, the plaque treatment portion of the second tube is made from an expandable material, such as an elastomeric polymer or mixture of elastomeric polymers. In some embodiments, the second tube is made from an expandable material along its entire length. In these embodiments the second tube can be formed from the same material and have the same dimensions from its proximal to distal end. For example, the second tube can be formed of the same polymeric material and have the same dimensions (wall thickness, inner and outer diameters) along the length of the tube.

In other embodiments, the plaque treatment portion of the second tube is formed of a different material composition than the other portions of the second tube (e.g., different than the proximal portion of the second tube). Alternatively, or in addition to a different material composition, the plaque treatment portion of the second tube can have a different dimension than the other portions of the second tube. For example, the plaque treatment portion can be fabricated from a material that is more highly expandable than material of the proximal portion of the second tube. This may be done by fabricating the plaque treatment portion with a polymer that is more highly elastomeric than the polymer of the second tube (e.g., using a polymer or polymer combination having a lower melting temperature than the rest of the tube). Alternatively, or in addition to a different material composition, the wall of the second tube at the plaque treatment portion may be thinner than the wall of the proximal portion of the second tube. The difference in material and/or thickness of the wall allows the second tube to be expanded with greater ease when force is applied to the inner surface of the second tube at the plaque treatment portion.

Exemplary outer diameters for the second tube are in the range of about 1 mm (3 Fr) to about 9.3 mm (28 Fr), about 2 mm (6 Fr) to about 4 mm (12 Fr), or about 4 mm (12 Fr) to about 8 mm (24 Fr). Exemplary inner diameters for the second tube are in the range of about 0.5 mm (1.5 Fr) to about 9 mm (1.5 Fr), about 1 mm (3 Fr) to about 8.7 mm (26 Fr), about 1.5 mm (4.5 Fr) to 3.3 mm (10 Fr), or about 3.3 mm (10 Fr) to about 7.5 mm (22.5 Fr). The wall thickness of the second tube can be in the range of about 35 μm to about 500 μm, or about 50 μm to about 1 mm. In embodiments wherein the wall thickness is reduced at the plaque treatment portion, the wall thickness may be reduced relative to areas outside the treatment portion of greater than 5%, such as about 5-75%, about 10-60%, or about 20-50%. For example, the wall thickness of the second tube in the plaque treatment portion can be in the range of about 5 μm to about 50 μm, about 25 μm to about 100 μm, or about 35 μm to about 200 μm.

The second tube can be formed from any material, or combination of materials, suitable for use within the body, wherein at least the plaque treatment portions are capable of expanding in response to pressure from the balloon.

The second tube can have a length suitable for the procedure being performed. In exemplary embodiments, the second tube has a length in the range of about 65 cm to about 200 cm. The second tube can have a length that is 5% greater, 10% greater, 20% greater or even in some cases 50% greater than the first tube depending upon the procedure being performed.

In many aspects materials used to form the second tube are compliant and flexible materials, and can include one or more elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The second tube can be made of a single elastomeric material, or a combination of materials. The second tube can be manufactured by an extrusion process, so that it is a single layer of material, or co-extruded to form a multi-layered material.

The material of the second tube can optionally be defined with regards to properties such as glass transition or crystalline melt temperatures. For example, material of the second tube, such as formed from one polymer, a copolymer or a polymer blends, can have a glass transition temperature in the range of about −40° C. to about 200° C., or more specifically, in the range of about −40° C. to about 14.4° C. (e.g., a Pellethane™ polyurethane elastomer).

In some embodiments, the plaque treatment portion of the second tube can be formed from a tubing material that has a lower glass transition or crystalline melt temperatures than another portion of the second tube (e.g., the proximal portion). The lower glass transition or crystalline melt temperature of the material can provide the plaque treatment portion with a greater degree of expandability. For example, the plaque treatment portion(s) of the second tube may have a glass transition or crystalline melt temperature that is at least about 15° C. lower, or at least about 40° C. lower than the glass transition or crystalline melt temperatures in areas of the second tube that are outside of the plaque treatment portion(s).

The second tube can also include one or more imaging material(s) to facilitate the location of one of more parts of the second tube during a medical procedure. The imaging materials (such as those materials described herein) can be applied to, or incorporated into, the second tube at one or more locations along its length include.

The "plaque treatment portion(s)" refers to one or more areas of the second tube along its distal portion that include one or more features (e.g., mechanical, pharmacological) useful for treating an arterial plaque. A plaque treatment portion may be defined by one or more parameters, such as by the function of the feature(s) that treat the plaque, the physical feature(s) of the plaque treatment portion (e.g., the material and configuration of the plaque scoring member), material features such as the presence of a coating material, bioactive agent feature(s) (e.g., a pharmacological agent), the area of the second tube that is covered with a feature useful for plaque treatment, and/or the location of a plaque treatment area on the second tube. In embodiments where the second tube includes more than one plaque treatment portion, the locations of the portions can be described in relation to one or more features of the second tube. Along the length of the second tube, a plaque treatment portion can begin where there is one or more plaque treatment feature(s) (e.g., a plaque scoring member, or drug delivery coating).

For example, a plaque treatment portion can occupy a length on the second tube that is useful for treating an arterial plaque. For example, a plaque treatment portion can have a length in the range of approximately a millimeter to approximately five or six centimeters. Exemplary lengths of the plaque treatment portion are in the range of about 1 mm to about 5 cm, about 2.5 mm to about 5 cm, about 5 mm to about 4 cm, about 7.5 mm to about 3 cm, or about 1 cm to about 2.5 cm. A plaque treatment portion can have proximal end and distal ends, wherein the proximal end is where the treatment portion starts along the length of the second tube, and the distal end is where the treatment portion ends.

If there are multiple plaque treatment portions, the portions can be the same or different lengths. Multiple plaque treatment portions can be defined by designations such as "$A_{2-20}$," "$B_{5-25}$" and "$C_{4-15}$", wherein treatment portion "A" is the treatment portion closest to the distal end and has a length in the range of 2-20 mm, treatment portion "B" is proximal to "A" and has a length in the range of 5-25 mm, and treatment portion "C" is proximal to "B" and has a length in the range of 4-15 mm. Alternatively, multiple treatment portions can be defined by the total of their lengths. For example, the second tube can have two treatment portions having a total length in the range of about 5 mm to about 100 mm, or can have three treatment portions having a total length in the range of about 15 mm to about 150 mm.

When there are multiple plaque treatment portions, the distance or distances between the plaque treatment portions can also be defined. For example, the distance between two plaque treatment portions can be greater than, equal to, or less than the length of an adjacent plaque treatment portion.

One or more types of plaque treatment feature(s) can be associated with one or more plaque treatment portion(s) as desired. For example, the second tube can have two or three plaque treatment portions, with each portion having a plaque scoring member (PSM). As another example, the second tube can have two or three plaque treatment portions, with each portion having a drug delivery coating (DDC). As another example, the second tube can have two or three plaque treatment portions, with each portion having a plaque scoring member and a drug delivery coating (PSM+DDC). Any combination of plaque scoring member (PSM) portion, drug delivery coating (DDC), and/or plaque scoring member and drug delivery coating (PSM+DDC) can be used, and their relative locations on the second tube can be described. The application contemplates various combinations of plaque scoring members with different functionalities, which can be arranged along the length of the second tube in a desired manner. Exemplary combinations of two types of plaque treatment portions are (i) A—PSM and B—DDC; (ii) A—DDC and B—PSM; (iii) A—PSM and B—PSM+DDC; (iv) A—DDC and B—PSM+DDC; (iv) A—PSM+DDC and B—DDC; (vi) A—PSM+DDC and B—PSM; wherein A is the most distal portion, and B is proximal to A. Exemplary combinations of three types of plaque treatment portions, include, but are not limited to: (i) A—PSM, B—DDC, and C—PSM; (ii) A—DDC, B—PSM, C—DDC; (iii) A—PSM, B—DDC, and C—PSM+DDC; (iv) A—DDC, B—PSM, and C—PSM+DDC; (v) A—PSM+DDC, B—PSM, C—DDC; and (vi) A—PSM+DDC, B—DDC, and C—PSM.

Figure 3A:
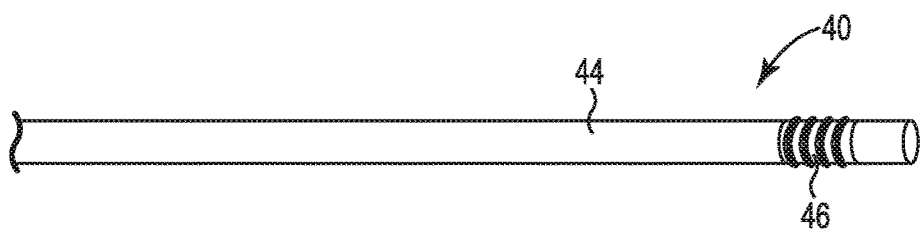
FIGS. 3A-3E are illustrations of various embodiments of the second tube with one or more different plaque treatment portions.
Figure 3B:
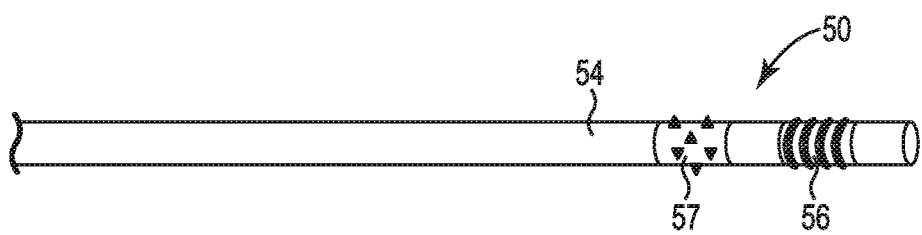
Figure 3C:
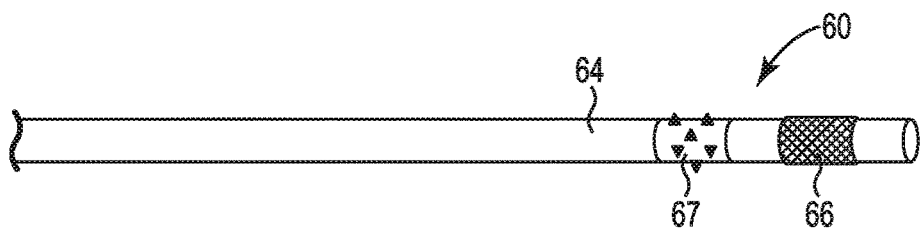
Figure 3D:
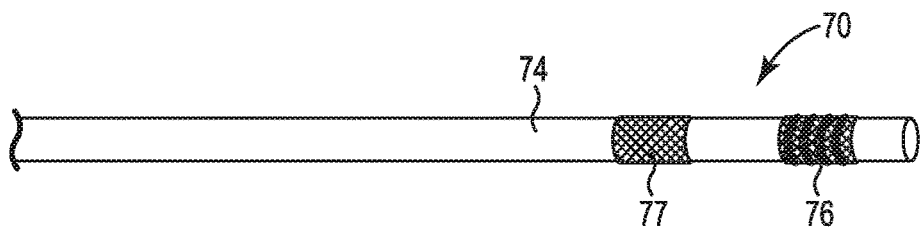
Figure 3E:
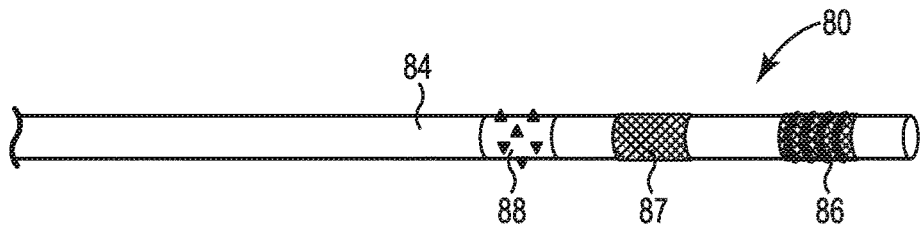

FIGS. 3A-3E illustrate various embodiments of the second tube having different plaque treatment portions. For example, FIG. 3A shows the distal end 40 of a second tube 44 of a plaque treatment system having a single plaque treatment portion 46 that has a scoring member. As another example, FIG. 3B shows the distal end 50 of a second tube 54 of a plaque treatment system having a two plaque treatment portions, which are a first plaque treatment portion 56 that has a scoring member, and second plaque treatment portion 57 that has a scoring member of a different configuration than the scoring member of the first plaque treatment portion 56. As another example, FIG. 3C shows the distal end 60 of a second tube 64 of a plaque treatment system having a two plaque treatment portions, which are a first plaque treatment portion 66 that has a drug delivery coating, and second plaque treatment portion 67 that has a scoring member. As another example, FIG. 3D shows the distal end 70 of a second tube 74 of a plaque treatment system having a two plaque treatment portions, which are a first plaque treatment portion 76 that has a scoring member and a drug delivery coating, and second plaque treatment portion 77 that has a drug delivery coating which is different than the first plaque treatment portion 76. As another example, FIG. 3E shows the distal end 80 of a second tube 84 of a plaque treatment system having a three plaque treatment portions, which are a first plaque treatment portion 86 that has a scoring member and a drug delivery coating, a second plaque treatment portion 87 that has a drug delivery coating which is different than the first plaque treatment portion 86, and a third plaque treatment portion 88 that has a scoring member of a different configuration than the scoring member of the first plaque treatment portion 86.

The disclosure also provides embodiments where the second tube has two or more plaque treatment portions, with one plaque treatment portion having a plaque scoring member of a first configuration or design, and another plaque treatment portion having a plaque scoring member of a second configuration or design. The different configurations can be reflected in differences in their abilities to treat plaques of varying degrees, such as the size of the plaque.

The disclosure also provides embodiments where the second tube has two or more plaque treatment portions, with one plaque treatment portion having a drug delivery coating with a first bioactive agent, and another plaque treatment portion drug delivery coating with a second bioactive agent. The different bioactive agents can be reflected in differences in their abilities to treat plaques.

Various designs and configurations of the plaque scoring member are contemplated. Generally, the plaque-scoring member comprises a raised portion comprising a hardened material that is able to abrade a plaque. With reference to plaque treatment, the term "abrade" or "score" refers to physically breaking up at least a portion of an arterial plaque.

The hardened material of the plaque treatment portion can be a biocompatible hard plastic or metal. Exemplary plastics include: acrylonitrile-butadiene-styrene (ABS), ethylene chlorotrifluoro ethylene copolymer (ECTFE), liquid crystal polymer (LCP), polyamide (PA), nylon 11 (PA 11), nylon 12 (PA 12), nylon 6 (PA 6), nylon 66 (PA 66), polaryl amide (PAA), polyamide imide (PAI), polybutylene terephthalate (PBT), polycarbonate (PC), polyethylene (PE), polyetheretherketone (PEEK), polyester imide (PEI), polyetherketone (PEK), polyether sulphone (PES), PET copolymer (PETG), polyethylene terephthalate (PETP), perfluoro alkoxyl alkane (PFA), polyimide (PI), polymethyl methacrylate (PMMA), polymethyl pentene (PMP), polyoxymethylene (POM), polypropylene (PP), polyphenylene ether (PPE), polyphenylene sulphide (PPS), polystyrene (PS), polysulphone (PSU), polytetrafluoroethylene (PTFE), and polyvinylidene flouride (PVDF).

Metals that can be used in the devices of the disclosure, such as in the plaque treatment portion of the devices, include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

The scoring member can have any configuration suitable for abrading a plaque. The scoring member can serve to scrape, cut, scratch, or abrade the plaque. In some configurations the scoring member can include one or more elongated structures, such as in the form of a small wire, filament, or rail, that is associated with the surface of the second tube. The elongated structure can be parallel to that axis of the second tube (catheter axis), perpendicular to the catheter axis, or at an angle to the catheter axis.

Figure 2:
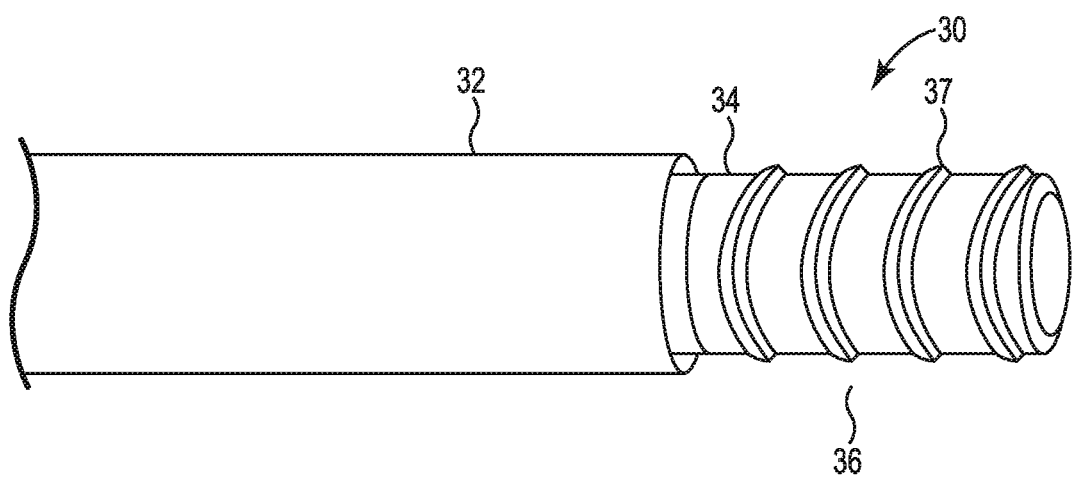
FIG. 2 is a perspective view of the distal end of a plaque treatment system with a plaque scoring member.

An example of an elongated structure that is at an angle to the catheter axis is one that is helically wrapped around the second tube at the plaque treatment portion. For example, FIG. 2 is a perspective view of the distal end 30 of a plaque treatment system. Shown is the first tube 32 and second tube 34 with plaque treatment portion 36 that has a helical scoring member 37. The helical scoring member 37 can be a hardened plastic or metal that can expand along with the second tube when an outward pressure is applied. When pressed up against a plaque, the scoring member 37 can cut into the calcified material in a process to remove plaque from the artery. In some modes of practice, the second tube 34 can be rotated with the scoring member 37 in contact with the plaque to exert an auger effect to facilitate plaque removal.

Figure 4:
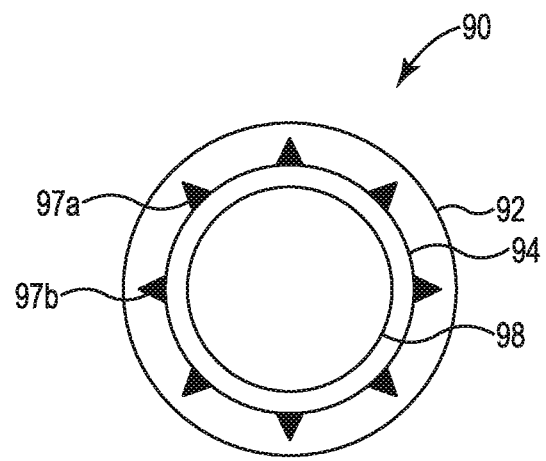
FIG. 4 is an illustration of a plaque treatment system as viewed from its distal end.

The plaque treatment portion can also include a plurality of elongated structures. A plurality of elongated structures can be parallel to each other, perpendicular to each other, or at angles to each other, or combinations thereof. As an example of an elongated structure, FIG. 4 shows a plaque treatment system 90 as viewed from its distal end. Shown is the first tube 92 and second tube 94 with plaque treatment portion that has a plurality of rails 97a, 97b, etc., that run parallel to the catheter axis and are arranged on the outer surface of the second tube 94. The rails are shown having a narrow portion (e.g., sharpened edge) at their outermost point. An expandable member 98, such as a balloon catheter, can be positioned within the second tube 94, and can cause the sharpened portions of the rails to cut into the plaque when the second member is expanded.

Figure 6:
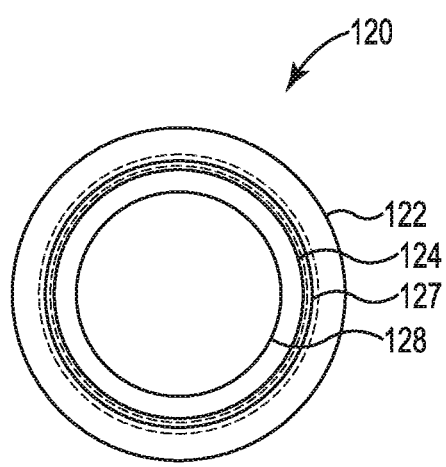
FIG. 6 is an illustration of a plaque treatment system as viewed from its distal end.
Figure 5A:
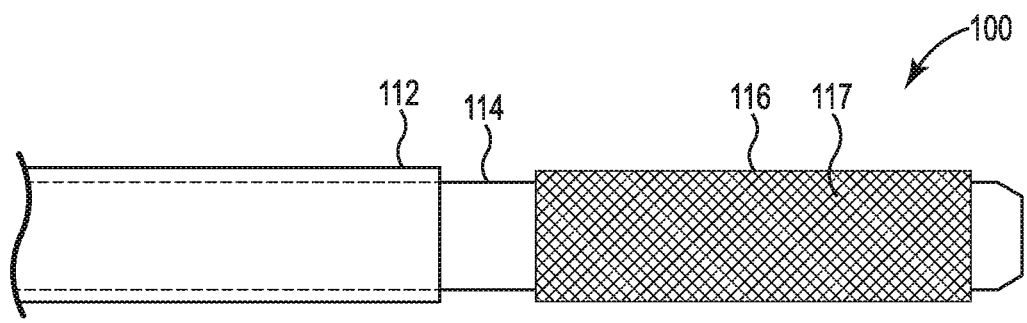
FIGS. 5A and 5B are illustrations of a plaque treatment system having a mesh structure in a non-expanded and expanded state, respectively.
Figure 5B:
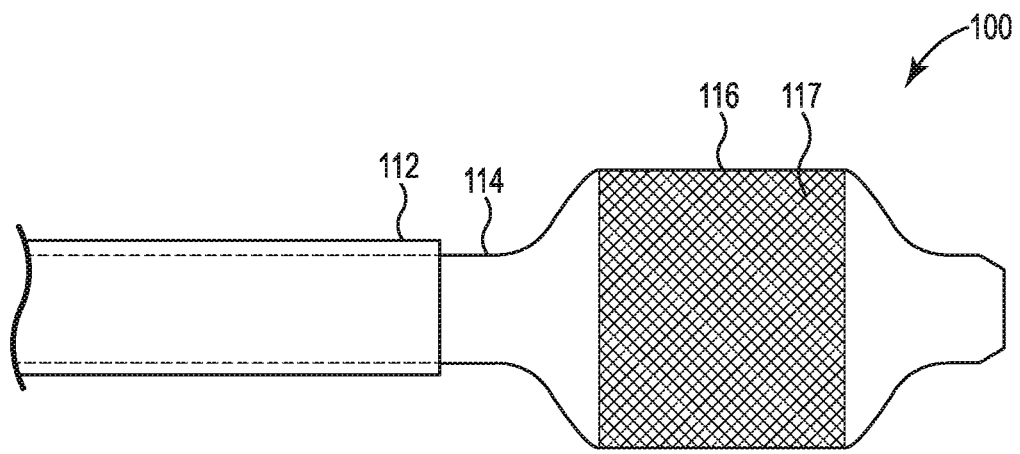

In other arrangements, the elongated structures are in the form of a grid-like or mesh-like structures. FIGS. 5A and 5B, and also FIG. 6 show illustrations of a grid-like or mesh-like structures. As show in FIG. 5A, the distal end 100 of a plaque treatment system is shown, with first tube 112, second tube 114 with plaque treatment portion 116, having a mesh structure 117 around the circumference of the second tube. As show in FIG. 5B, upon expansion of the expandable member (not shown), such as a balloon within the second tube, the second tube can bulge outward causing the mesh structure 117 to expand with it. The overall length of the plaque treatment portion 116, including the mesh structure 117, may shorten. FIG. 6 is a plaque treatment system 120 having a plaque treatment portion with mesh structure, as viewed from its distal end. Shown is the first tube 122 and second tube 124 with plaque treatment portion that has a mesh structure 127 around the circumference of the second tube 124. An expandable member 128, such as a balloon catheter, can be positioned within the second tube 124, and can cause the mesh structure to expand at the treatment site and abrade the plaque.

In other embodiments, the scoring member can be in the form of one or more spikes, barbs, posts, or the like. The spikes can project from the surface of the second tube. Spike projections from the surface of a plaque scoring member can be seen in FIG. 3B (second plaque treatment portion 57), and FIG. 3E (third plaque treatment portion 88).

All or a portion of the scoring member may be attached to the surface of the second tube at one or more points in the plaque treatment area. For example, in some constructions an adhesive can be used to attach the scoring member to the surface of the second tube. In other constructions the scoring member can be attached to the surface of the second tube using a heat molding or melting process. For example, the distal portion of the second tube can be formed by heat molding the scoring member to the surface.

In some embodiments, bioactive agent is associated with the plaque treatment portion. The bioactive agent can be releasably associated with the plaque treatment portion, or non-releasably associated with the plaque treatment portion in a manner that it presents bioactive agent to body tissue. In some embodiments the plaque treatment portion comprises a coating that can modulate the release of bioactive agent. For example, the bioactive agent can be present within and releasable from a matrix of polymeric material coated on the surface of the second tube. A polymeric coating may also be applied over a drug or drug containing layer to serve as a top coat which modulates the release of the bioactive agent.

Exemplary bioactive agents include, but are not limited to, antibiotics, anti-inflammatory agents, anti-proliferative agents, immunomodulatory agents, anti-mitotics and anesthetics. Examples of bioactive agents that could be released or presented from the plaque treatment portion of the second tube include sirolimus (rapamycin), analogs of rapamycin ("rapalogs"), tacrolimus, everolimus, zotarolimus, temsirolimus, pimecrolimus, ridaforolimus, paclitaxel, taxane, dexamethasone, betamethasone, paclitaxel, vinblastine, vincristine, vinorelbine, poside, teniposide, dactinomycin (actinomycin D), daunorubicin, doxorubicin, idarubicin, anthracyclines, mitoxantrone, bleomycins, plicamycin (mithramycin), mitomycin, mechlorethamine, cyclophosphamide and its analogs, melphalan, chlorambucil, ethylenimines and methylmelamines, alkyl sulfonates-busulfan, nirtosoureas, carmustine (BCNU) and analogs, streptozocin, trazenes-dacarbazinine, methotrexate, fluorouracil, floxuridine, cytarabine, mercaptopurine, thioguanine, pentostatin, 2-chlorodeoxyadenosine, cisplatin, carboplatin, procarbazine, hydroxyurea, mitotane, aminoglutethimide, estrogen, heparin, synthetic heparin salts, tissue plasminogen activator, streptokinase, urokinase, aspirin, dipyridamole, ticlopidine, clopidogrel, abciximab, breveldin, cortisol, cortisone, fludrocortisone, prednisone, prednisolone, 6U-methylprednisolone, triamcinolone, aspirin, acetaminophen, indomethacin, sulindac, etodalac, tolmetin, diclofenac, ketorolac, ibuprofen and derivatives, mefenamic acid, meclofenamic acid, piroxicam, tenoxicam, phenylbutazone, oxyphenthatrazone, nabumetone, auranofin, aurothioglucose, gold sodium thiomalate, cyclosporine, tacrolimus (FK-506), azathioprine, mycophenolate mofetil, vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

Other exemplary embodiments of bioactive agents include, but are not limited to, bioactive agents for treatment of hypertension (HTN), such as guanethidine.

In a particular embodiment, the bioactive agents are selected from the group consisting of paclitaxel, sirolimus (rapamycin) and mixtures thereof.

In embodiments wherein the plaque treatment portion includes a polymer, the polymer can be bio-stable or bio-degradable, organic or inorganic, or a synthetic or naturally-occurring substance. The polymeric material can be selected from a variety of polymeric materials. In some cases, the polymeric material is selected to incorporate a desirable amount of the bioactive agent, and to either retain the bioactive agent so that it is sufficiently presented to the surrounding physiological environment, or to release the bioactive agent. For example, bio-stable polymers can be permeable to the bioactive agent, which can be released by diffusion through and out of the polymeric material.

Bio-stable polymeric materials include, but are not limited to, polyurethanes, polyethylenes, polyethylene teraphthalates, ethylene vinyl acetates, silicones, polyethylene oxide, and poly(alkyl(meth)acrylates), such as poly(n-butyl methacrylate). Exemplary polymers include poly(ethylene-co-vinyl acetate); poly(ethylene-co-alkyl acrylates), such as poly(ethylene-co-methyl acrylate), poly(ethylene-co-ethyl acrylate) and poly(ethylene-co-butyl acrylate); polyisobutylene and copolymers of the butene monomers; and epichlorohydrin-containing polymers, such as polyepichlorohydrin and poly(epichlorohydrin-co-ethylene oxide).

In some embodiments, bioactive agent is associated with the plaque treatment portion, and the bioactive agent is within, or in the form of microparticulates, that are associated with the plaque treatment portion. When the second tube is expanded, the microparticulates can be released or dissociated from the plaque treatment surface. In some modes of practice, the microparticulates are associated with a coating on the surface of the second tube. Exemplary coatings include those including hydrophilic polymers, and those including degradable polymers. Following release from the plaque treatment portion of the second tube, the microparticulates can become associated with tissue and release bioactive agent.

In one embodiment, the plaque treatment portion comprises a flexible hydrogel coating and microparticulates associated with the flexible hydrogel coating. The microparticulates may be associated with the coating in a non-homogenous manner, for example, the microparticulates can be associated with the flexible hydrogel coating (a) near the surface of the flexible hydrogel, coating, (b) predominantly near the flexible hydrogel coating/surface of the second tube, or (c) homogenously distributed in the flexible hydrogel coating. Upon visualization, microparticulates that are marginally embedded in a flexible hydrogel coating may appear to be stuck to the coating surface.

The microparticulates are the particulate components that include bioactive agent, and which are releasable from the surface of the second tube at a plaque treatment portion. The microparticulates can be any three-dimensional particle having a size (e.g., in the range of about 100 nm to about 10 μm) and shape (spherical, or substantially spherical, non-spherical shapes or irregular shape, such as rod-like, filament-like, sliver-like, or needle-like shapes) sufficient to be associated with the second tube via coating materials, and then dissociated upon its expansion of the substrate.

Microparticulates that are formed solely of one or more bioactive agents can be associated with the surface of the second tube at the plaque treatment portion released to target tissue in vivo. In other words, the microparticulates can be formed substantially or entirely of one or more bioactive agents, and an excipient substance that may otherwise control release of the bioactive agent from the microparticulates is not required. A microparticulate that is formed entirely or almost entirely (e.g., allowing for trace amounts of one or more other components) of a bioactive agent may be referred to herein as a "neat" microparticulate.

For example, the preparation of paclitaxel microparticles has been described in U.S. Pat. No. 6,610,317. Commonly assigned U.S. application Ser. No. 14/280,054 (U.S. 2014/0343491; Slager) and U.S. application Ser. No. 14/303,309 (U.S. 2015/0017219; Slager et al.) describes the preparation of macrolide particulates having desirable shapes and sizes using various solvent(s) and/or processing techniques.

One class of hydrophilic polymers useful as polymeric materials for a hydrophilic coating, such as a hydrophilic base coat, is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,Ndimethylaminopropylmeth-acrylamide) are described in example 2 of U.S. Pat. No. 7,807,750 (Taton et al.), the disclosure of which is incorporated herein by reference.

Other hydrophilic polymers that can be useful in the present disclosure are derivatives of acrylamide polymers with photoreactive groups. One such representative hydrophilic polymer can be the copolymerization of N-[3-(4-benzoylbenzamido)propyl]methacrylamide (Formula I) with N-(3-aminopropyl)methacrylamide (Formula II) to produce the polymer poly(N-3-aminopropyl)methacrylamide-co-N-[3-(4-benzoylbenzamido)propyl]methacrylamide (Formula III). The preparation of the polymer is disclosed in Example 1 of US Patent Publication 2007/0032882 (to Lodhi, et al.), the full content of which is incorporated herein by reference.

Formula I

Formula II

Formula III

In some embodiments, the hydrophilic polymer can be a vinyl pyrrolidone polymer, or a vinyl pyrrolidone/(meth) acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth) acrylamide derivatives, such as alkyl(meth)acrylamide, as exemplified by dimethylacrylamide, and aminoalkyl(meth) acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Pat. No. 7,807,750 (Taton et al.).

In embodiments, polymers and copolymers that can be used in coatings in device embodiments of the disclosure are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. Aryl ketones herein can specifically include diaryl ketones. Polymers herein can provide a hydrophilic polymer having a pendent activatable photogroup that can be applied to the expandable and collapsible structure, and can then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of a portion of the surface of the device, such as a plaque treatment portion of the second tube.

A hydrophilic polymer having pendent photoreactive groups can be used to prepare a flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Hydrophilic photo-polyacrylamide polymers such as poly(acrylamide-co-N-(3-(4-benzoylbenzamido)propyl)methacylamide), "Photo-PAA", and derivatives thereof can be used to form hydrophilic base coats in exemplary embodiments of the present disclosure. Methods for the preparation of photo-polyacrylamide are described in U.S. Pat. No. 6,007,833, the disclosure of which is incorporated herein by reference.

Other embodiments of hydrophilic base coats include derivatives of photo-polyacrylamide polymers incorporating additional reactive moieties. Some exemplary reactive moieties include N-oxysuccinimide and glycidyl methacrylate. Representative photo-polyacrylamide derivatives incorporating additional reactive moieties include poly(acrylamide-co-maleic-6-aminocaproic acid-N-oxysuccinimide-co-N-(3-(4-benzoylbenzamido)propyl) methacrylamide) and poly(acrylamide-co-(3-(4-benzoylbenzamido)propyl) methacrylamide)-co-glycidylmethacrylate. Additional photo-polyacrylamide polymers incorporating reactive moieties are described in U.S. Pat. No. 6,465,178 (to Chappa, et al.), U.S. Pat. No. 6,762,019 (to Swan, et al.) and U.S. Pat. No. 7,309,593 (to Ofstead, et al.), the disclosures of which are herein incorporated by reference.

Other embodiments of exemplary hydrophilic base coats that include derivatives of photo-polyacrylamide polymers incorporating additional reactive moieties can be found in U.S. Pat. No. 6,514,734 (to Clapper, et al.), the disclosure of which is incorporated herein by reference in its entirety.

In yet other embodiments, the hydrophilic base coat can include derivatives of photo-polyacrylamide polymers incorporating charged moieties. Charged moieties include both positively and negatively charged species. Exemplary charged species include, but are not limited to, sulfonates, phosphates and quaternary amine derivatives. Some examples include the negatively charged species N-acetylated poly(acrylamide-co-sodium-2-acrylamido-2-methylpropanesulfonate-co-N-(3-(4-benzoylbenzamido)propyl) methacrylamide)-co-methoxy poly(ethylene glycol) monomethacrylate. Other negatively charged species that can be incorporated into the hydrophilic base coat are described in U.S. Pat. No. 4,973,993, the disclosure of which is incorporated herein by reference in its entirety. Positively charged species can include poly(acrylamide-co-N-(3-(4-benzoylbenzamido)propyl)methacrylamide)-co-(3-(methacryloylamino)propyl)trimethylammonium chloride. Other positively charged species that can be incorporated into the hydrophilic base coat are described in U.S. Pat. No. 5,858,653 (to Duran et al.), the disclosure of which is incorporated herein by reference in its entirety.

Polymers and copolymers that can be used with device embodiments of the disclosure can be derivatized with one or more polymerizable group(s). Polymers with pendent polymerizable groups are commonly referred to as macromers. The polymerizable group(s) can be present at the terminal portions (ends) of the polymeric strand or can be present along the length of the polymer. In one embodiment polymerizable groups are located randomly along the length of the polymer.

Exemplary hydrophilic polymer coatings can be prepared using polymer grafting techniques. Polymer grafting techniques can include applying a nonpolymeric grafting agent and monomers to a substrate surface then causing polymerization of the monomers on the substrate surface upon appropriate activation (for example, but not limited to, UV radiation) of the grafting agent. Grafting methods producing hydrophilic polymeric surfaces are exemplified in U.S. Pat. Nos. 7,348,055; 7,736,689 and 8,039,524 (all to Chappa et al.) the full disclosures of which are incorporated herein by reference.

Optionally, a coating on a device of the disclosure can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used in association with device embodiments of the disclosure. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Crosslinking agents can include those having formula Photo¹-LG-Photo², wherein Photo¹ and Photo² independently represent at least one photoreactive group and LG represents a linking group comprising at least one silicon or at least one phosphorus atom. A degradable linking agent can include a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

Crosslinking agents including at least two photoreactive groups can be used in association with device embodiments of the disclosure. Exemplary crosslinking agents are described in U.S. Pat. No. 8,889,760, the content of which is herein incorporated by reference in its entirety.

In some embodiments, a crosslinking agent having a molecular weight of less than about 1500 kDa can be used in association with device embodiments of the disclosure. In some embodiments the crosslinking agent can have a molecular weight of less than about 1200, 1100, 1000, 900, 800, 700, 600, 500, or 400.

In some embodiments, a crosslinking agent comprising a linking agent having formula Photo¹-LG-Photo² can be used in association with device embodiments of the disclosure. Photo¹ and Photo², independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, device embodiments of the disclosure can be associated with a crosslinking agent comprising a linking agent having a formula selected from:

(a)
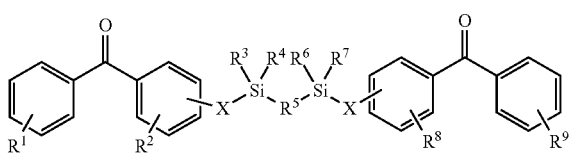

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)
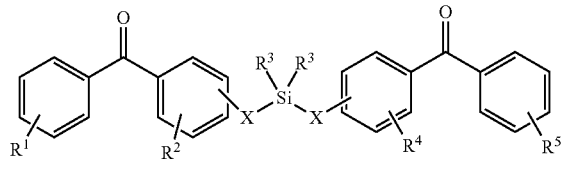

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)
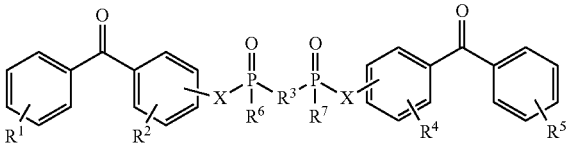

wherein R1, R2, R4 and R5 are any substitution; R3 is any substitution; R6 and R7 are alkyl, aryl, or a combination thereof; and each X can independently be O, N, Se, S, alkylene, or a combination thereof; and (d)
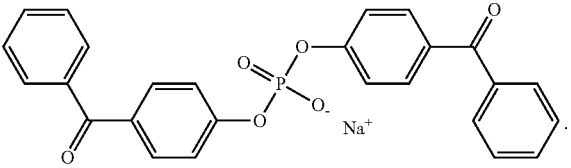

In a particular embodiment, the crosslinking agent can be bis(4-benzoylphenyl) phosphate.

In some embodiments, an ionic photoactivatable crosslinking agent having good solubility in an aqueous composition can be used in association with device embodiments of the disclosure. In some cases, the ionic photoactivatable crosslinking agent can crosslink the polymers within a coating layer which can also improve the durability of the coating.

Any suitable ionic photoactivatable crosslinking agent can be used. In some embodiments, the ionic photoactivatable crosslinking agent is a compound of formula I: $X_1—Y—X_2$ where Y is a radical containing at least one acidic group, basic group, or a salt of an acidic group or basic group. $X_1$ and $X_2$ are each independently a radical containing a latent photoreactive group. The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/mL. In some embodiments, the solubility is about 0.1 to about 10 mg/mL or about 1 to about 5 mg/mL.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammoniumsalt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

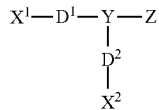

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Additional exemplary degradable ionic photoactivatable crosslinking agents are described in U.S. Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula $XR_1R_2R_3R_4$, where X is a chemical backbone, and $R_1$, $R_2$, $R_3$, and $R_4$ are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

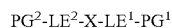

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Exemplary non-ionic photoactivatable crosslinking agents can also include, for example, those described in U.S. Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula $R^1$—X—$R^2$, wherein $R^1$ is a radical comprising a vinyl group, X is a radical comprising from about one to about twenty carbon atoms, and $R^2$ is a radical comprising a photoreactive group.

A single photoactivatable crosslinking agent or any combination of photoactivatable crosslinking agents can be used in forming a coating associated with device embodiments of the disclosure. For example, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis (4-benzoylbenzyldi-methylammonium) salt or at least one anionic photoactivatable crosslinking agent such as 4,5-bis (4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Publ. Pat. App. No. 2010/0274012 (to Guire et al.) and U.S. Pat. No. 7,772,393 (to Guire et al.) the content of all of which is herein incorporated by reference.

A coating associated with device embodiments of the disclosure can include boron-containing linking agents such as boron-containing linking agents disclosed in U.S. Pat. Publication 2013/0302529 ("Boron-Containing Linking Agents;" Kurdyumov et al.), the content of which is herein incorporated by reference. By way of example, linking agents can include borate, borazine, or boronate groups and coatings and devices that incorporate such linking agents, along with related methods. In an embodiment, the linking agent includes a compound having the structure (I):

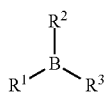

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

Additional agents for use with device embodiments herein can include stilbene-based reactive compounds including, but not limited to, those disclosed in U.S. Pat. No. 8,487,137, entitled, "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

Natural polymers can also be used to form a hydrophilic coating which can be associated with device embodiments of the disclosure. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In some instances a tie layer can be associated with device embodiments of the disclosure, such as a tie layer used with a hydrophilic coating. In some instances a tie layer can be added to a hydrophilic base layer. The tie layer can act to increase the adhesion of the hydrophilic base layer to the substrate. In some embodiments, a tie layer can act to increase adhesion of the hydrophobic active agent to the hydrophilic base layer. Exemplary ties layers include, but are not limited to silane, butadiene, polyurethane and parylene. Silane tie layers are described in US Patent Publication 2012/0148852 (to Jelle, et al.), the content of which is herein incorporated by reference.

In exemplary embodiments, the hydrophilic base layer can include tannic acid, polydopamine or other catechol containing materials.

In some embodiments, when a plaque treatment portion is placed proximal to a treatment site, and the balloon is inflated to expand second tube the microparticulates can be released from the coating. In cases where a flexible hydrogel matrix is used, it may be hydrated by body fluids which can cause the matrix material to loosen around the microparticulates. Expansion of the plaque treatment portion of the second tube can cause it to bulge and push the flexible hydrogel coating up against the arterial plaque. The hydration and loosening of the flexible hydrogel coating along with the expansion of the second tube can facilitate release of the microparticulates from the coating.

In some cases, the coating may deform to a point where the microparticulates are no longer entrapped and can be released from the coating. For example, upon expansion, the coating may thin sufficiently to release the microparticulates. Alternatively, or additionally, the coating may expand to a point where pores are created in the expanded coating sufficient in size to release the microparticulates. Microparticulates are transferred to the arterial plaque of the subject, and bioactive agent can be released to provide a therapeutic effect.

After microparticulate transfer to the plaque has taken place the balloon can be deflated causing contraction of plaque treatment portion of the second tube. The flexible hydrogel coating can pull away from the plaque, leaving the microparticulates associated with the plaque. Methods of the invention can provide a transfer of microparticulates to tissue in the range of about 10% to 100%, or more desirably in the range of about 30% to 100%.

In other embodiments, the plaque treatment portion can have a biodegradable coated layer which facilitates association of the microparticulates with the second catheter tube.

The device can include a degradable coated layer present between the microparticulates and the surface of the second tube. The degradable coated layer can be present as a base coat on the surface of the second tube. The degradable coated layer can cause association of the microparticulates with the second tube, for example, by adhesive properties of the polymeric materials that are used to form the layer with the microparticulates. In another aspect microparticulates are embedded in, or covered with, a biodegradable coating formed on the second tube. In a non-expanded state, the microparticulates are substantially or entirely entrapped in the coating, or covered by the coating. Upon expansion of the second tube the biodegradable coating can fracture and delaminate from the surface which can cause release of portions of the coating along with the microparticulates. The delaminated biodegradable fragments with microparticulates can be transferred to tissue of the subject. The delaminated biodegradable fragments can have a greater adhesivity to the tissue than to the substrate. In some cases the degradable coated layer between the microparticulates and the surface of the second tube can erode, facilitating release of the microparticulates. The microparticulates can become released at the target site, along with expansion of the substrate.

The microparticulates that are transferred can adhere to the arterial tissue at the target site. Accordingly, the microparticulates can release bioactive agent at the target site, which can have a therapeutic effect on the tissue. The release of the drug at the target site can be useful to control tissue response after balloon dilation. For example, the microparticulates can release an antiproliferative agent, such as sirolimus or paclitaxel that can inhibit neointimal proliferation at the dilated site. As another example, the microparticulates can release an antithrombotic agent, such as heparin, that can inhibit clotting.

The expandable member can be any device that is able to exert pressure against the inner surface of the second tube to expand it outwards at the plaque treatment portion. In some embodiments the expandable member can be a structure that is outwardly biased, but is otherwise kept in a constricted state when moved through the second tube prior to expansion.

In some embodiments, the expandable member of the system comprises a balloon catheter. Balloon catheters are commonly used in angioplasty procedures for the treatment of arteries that are diseased. Balloon angioplasty generally involves the dilation or reopening of blocked intraluminal channels. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. A balloon catheter generally includes four portions: the balloon, catheter shaft, guidewire, and manifold. An elongated catheter shaft with the inflatable balloon can be attached to a distal section of the catheter shaft. At a proximal end of the catheter shaft, there is typically a manifold. At the manifold end, placement of the catheter can be facilitated using a guidewire. Guidewires are small and maneuverable and can facilitate movement of the balloon catheter within the second tube. In some arrangements, the balloon and catheter is fixed to the guidewire, which can be moved together with the guidewire. In other arrangements, the balloon and catheter are not fixed to the guidewire can be moved over a guidewire within the second tube.

The balloon can be inserted into the second tube and advanced through the tube in an unexpanded state. For example, in some modes of practice the guidewire is moved to a location in the second tube at a plaque treatment portion, and the catheter with balloon portion is then fed over the guidewire until the balloon reaches the treatment portion in the second tube. The balloon can then be inflated to thereby apply the requisite mechanical force to the inner wall of the second tube at the plaque treatment portion, thereby causing expansion of the second tube and in turn forcing the outer surface, which includes the plaque treatment member, up against the plaque of the arterial wall, thereby providing treatment. The manifold can also control the fluid introduction within shaft for expansion of the balloon.

The balloon is typically inflated using a fluid, which is injected through an inflation port. The mechanics of fluid transfer and introduction within balloons vary according to the specific design of the catheter, and are well known in the art.

Exemplary thicknesses for the walls of catheter balloons are in the range of about 5 μm to about 20 μm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon. In some cases, a balloon with a thick wall is used, to provide for a higher pressure rating which can be useful in expanding the second tube at the plaque treatment portion.

As an alternative to a balloon of a balloon catheter as the expandable member, the system can include a self-expanding stent (or cage or sleeve) to exert force against the inner surface of the second tube to expand it outwards at the plaque treatment portion. The self-expanding stent can be controlled by a wire used in conjunction with the system.

Know diagnostic procedures can be used to identify a patient in need of treatment of one or more arterial plaques. Noninvasive imaging techniques such as computed tomography (CT), magnetic resonance imaging (MRI), and nuclear imaging can be used to image the heart and evaluate coronary arteries. CT imaging, for example, can provide information about the location and composition of coronary atherosclerotic plaque(s) in a patient. In particular electron beam computed tomography (EBCT) and multidetector computed tomography (MDCT) are two similar methods that can be used for the visualization and quantification of coronary artery calcification.

Once information about the one or more plaques is known, the system of the disclosure having one or more plaque treatment portion(s) can be chosen to most effectively treat the plaque(s). For example, based on the imaging information, the type and size of the plaque treatment portion(s) can be chosen to provide the most appropriate and effective therapy.

The system with the second tube having one or more plaque treatment portion(s) can be used for the treatment of diseased arteries to reduce atherosclerotic stenosis or to recanalize occluded arteries. The plaque treatment portion of the second tube can be used in a manner similar to use of a balloon catheter in a balloon angioplasty procedure. Balloon angioplasty is commonly carried out for the treatment of diseased arteries to reduce atherosclerotic stenosis or to recanalize occluded arteries. In balloon angioplasty, obstructed intraluminal passages can be reopened or dilated by inflation of the balloon at the occluded site. The current system and method can provide at least the same effect using one or more plaque treatment portion(s) of the second tube.

According to embodiments of the disclosure, the system including the first tube, second tube, and expansion member (e.g., balloon catheter) can be inserted percutaneously into a vessel (e.g. artery) of a patient. These components can be inserted into the vessel in any desired manner. For example, in one mode of practice, the first tube is inserted into the vessel, followed by insertion of the second tube and the balloon catheter. The balloon catheter can be inserted along with the second tube, or the second tube can be inserted into the first tube, subsequently followed by insertion of the balloon catheter into the second tube. Alternatively, the first tube, second tube, and expansion member can be inserted into the vessel simultaneously.

The first tube, second tube, and balloon catheter can be advanced to a treatment site where there is one or more arterial plaques. At the plaque site, the first catheter tube or second catheter tube can be moved to expose the plaque treatment portion of the second tube to the treatment site (e.g., an arterial plaque). For example, in some modes of practice, the distal end of the first tube is moved to, or beyond, a plaque to be treated. The distal end of the second tube is provided at or near the distal end of the first tube with the plaque treatment portion being aligned with the plaque to be treated. Next, the first tube is withdrawn (i.e., moved proximally) to uncover the plaque treatment portion of the second tube which is positioned at the plaque. The balloon portion of the balloon catheter can then be positioned within the second tube at the plaque treatment portion, and then inflated to cause extension of the plaque treatment portion up against the plaque. An abrasion member or a bioactive agent, or both, of the plaque treatment portion can treat the plaque. After the plaque is abraded the balloon can be deflated, and the second tube can be moved proximally back within the first tube.

In another mode of practice, a single plaque can be treated with a first plaque treatment portion having a plaque scoring member that abrades the plaque, and then with a second plaque treatment portion that treats the abraded plaque with a bioactive agent that is released from a coating. In an exemplary mode of practice, the distal end of the first tube is moved beyond a plaque to be treated, where a first plaque treatment portion having scoring member is aligned with the plaque, and a second plaque treatment portion having a bioactive agent is distal to the plaque. Next, the first tube is withdrawn (i.e., moved proximally) to uncover the first plaque treatment portion and the balloon then inflated to cause abrasion of the plaque. The balloon is then deflated. Next, the second tube is moved proximally to position the second plaque treatment portion by the abraded plaque, and the balloon is positioned within the second tube at the second plaque treatment portion. The balloon is then inflated so the bioactive agent-containing surface of the second plaque treatment portion presses up against the abraded plaque and bioactive agent is released. The balloon can then be deflated and the second tube moved proximally back into the first tube.

In yet other modes of practice, two or more plaques may be subject to treatments with two or more different plaque treatment portions. For example, a first plaque can be treated with a first plaque treatment portion, and then a second plaque can be treated with a second plaque treatment portion.

Figure 7A:
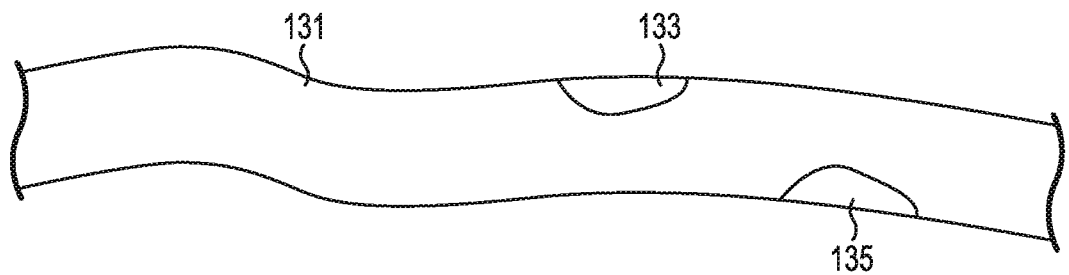
FIGS. 7a-7d illustrate placement of components of the system in an artery of a subject to treat arterial plaques.
Figure 7B:
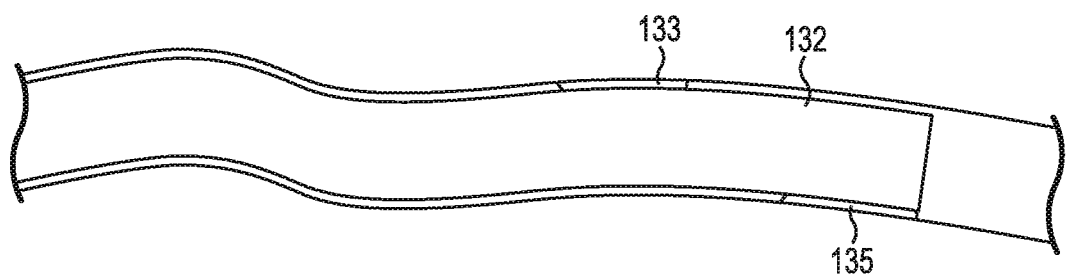
Figure 7C:
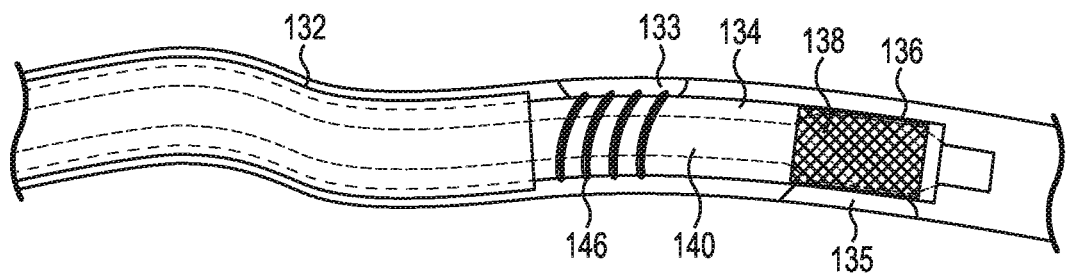
Figure 7D:
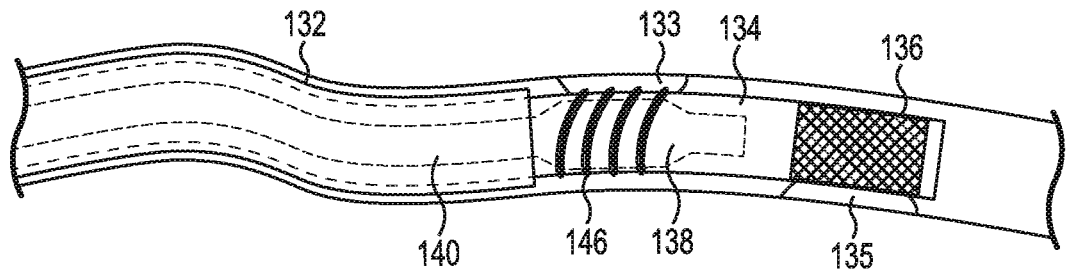

Reference is made to FIGS. 7a-7d, showing exemplary modes of placing components of the system to treat arterial plaque using two plaque treatment portions. FIG. 7a shows a portion of an artery 131, with first 133 and second 135 sites of plaque accumulation. In one mode of practice and with reference to FIG. 7b, first tube 132 is inserted into the artery 131 distal to the first 133 and second 135 sites of plaque accumulation. This can be followed by insertion of the second tube and the balloon catheter (not shown in FIG. 7b), or the second tube/balloon catheter can be inserted along with the first tube. With reference to FIG. 7c, and with the system component placed at the treatment sites, the first tube 132 can be withdrawn (moved proximally) past the first 133 and second 135 sites of plaque accumulation. This exposes the second tube 134 with second plaque treatment portion 136 having a drug delivery coating to the second plaque site 135, and also exposes the first plaque treatment portion 138 having a plaque scoring member to the first plaque site 133. FIG. 7c also shows a balloon catheter within the second tube 134, the balloon catheter having an inflatable balloon portion 138 and a catheter portion 140, with the balloon portion 138 positioned within the second plaque treatment portion 136 at the second plaque site 135. The balloon portion can be inflated to expand the second tube thereby pressing the drug delivery coating up against the second plaque thereby delivering drug (inflation not shown). Next, as shown in FIG. 7d, the balloon catheter is moved proximally within the second tube 134, to position the balloon portion 138 within the first plaque treatment portion 146 at the first plaque site 133. The balloon portion can be inflated to expand the second tube thereby pressing the scoring member up against the first plaque and causing its abrasion (inflation not shown).

Optionally, the balloon of the expansion member can be moved distally out of the second tube to provide further or alternative bioactive vessel treatment to treatment provided by the second tube. Exemplary methods can include (i) dilatation of the vessel using the balloon of the expansion member moved distally beyond the distal end of the second tube; (ii) deflation of the balloon of the expansion member; (iii) proximal retraction of the balloon into the second tube; and (iv) inflation of the balloon of the expansion member, thus delivering bioactive from the surface of the second tube.

In another embodiment, the disclosure provides a plaque treatment catheter assembly having a catheter tube with proximal and distal catheter ends, and inner and outer surfaces defining a catheter wall and an inner diameter of the catheter tube, with the catheter tube configured for insertion within the vasculature. In the catheter tube there are one or more channel(s) within the catheter wall that are parallel to an axis of the catheter tube, with the channel(s) extending from the proximal to distal end of the catheter tube. The assembly also includes one or more elongate member(s) having a distal portion comprising a plaque scoring element or a clot retrieval member, or both, and a portion proximal to the distal portion configured to move within the channel. The assembly also includes an expandable member that is movable within and out of the inner diameter of the catheter tube. The expandable member can be a balloon portion of a balloon catheter, or a self-expanding tubular structure (such as an expanding cage or stent), that can be expanded to cause movement of the scoring element.

Figure 8:
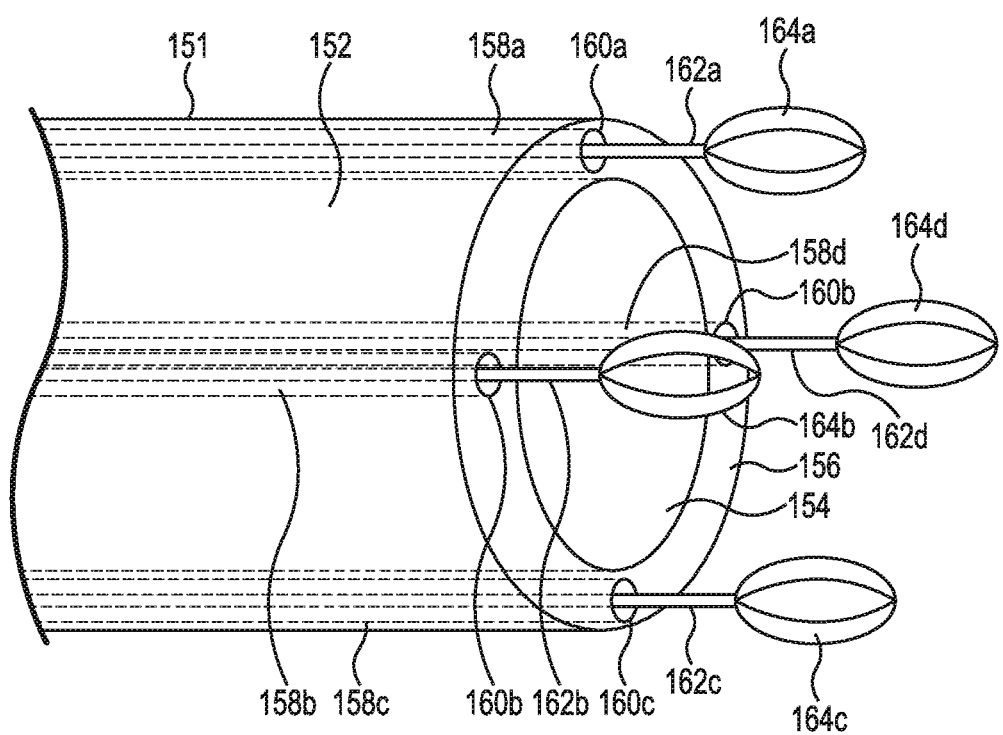
FIG. 8 is a perspective view of the distal end of an embodiment of a plaque treatment system with plaque scoring members.

Reference is made to FIG. 8 showing the distal end of the catheter assembly 150, with catheter tube 151 having outer surface 152 and inner surface 154, which define a catheter wall 156. Within the catheter wall are channels 158a, 158b, 158c, and 158d. Although four channels are shown, the catheter tube can have any desired number of channels, such as 1, 2, 3, 4, 5, 6, etc., channels. If the catheter tube includes two or more channels, they can be spaced out in any desired manner, such as with equal spacing (as shown in FIG. 8), or unequal spacing. The channels extend from their respective apertures (160a, 160b, 160c, and 160d) at the distal end of the catheter tube 151 and through the length of the tube to the proximal end (not shown).

The catheter assembly 150 assembly also includes one or more elongate member(s) that are configured to move within the channel(s). In one embodiment, as shown in FIG. 8, the elongate members include a portion (162a, 162b, 162c, and 162d) configured to reside and be movable within the channel, which can be formed of a flexible wire, cord, or rod, such as one made from a biocompatible metal or polymeric material. The wire can be very thin such as having a diameter of about 0.05 mm, about 0.1 mm, about 0.2 mm, or about 0.5 mm, or greater. The channel the wire is movable in can have a cross sectional distance (e.g. diameter) that is greater than the diameter of the wire, such as about 1.5-4 times the diameter of the wire. Although the channels is shown as having a circular shape as viewed from the end of the tube, the channel can have any shape (e.g, oval or polygonal) suitable for accommodating and allowing movement of the wire.

Figure 9A:
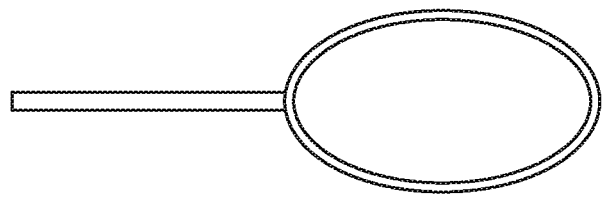
FIGS. 9A-9D are illustrations of various embodiments of the plaque scoring members.
Figure 9B:
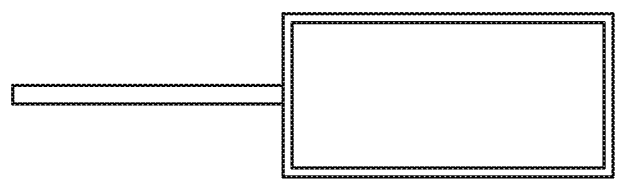
Figure 9C:
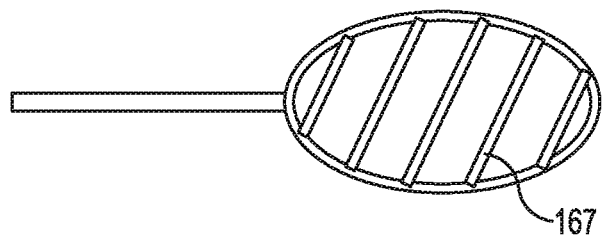
Figure 9D:
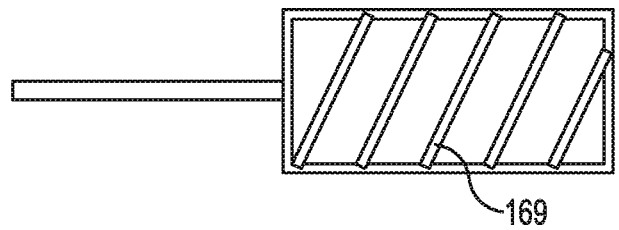

Also shown in FIG. 8, at the distal end of the elongate member(s) are plaque scoring element(s) (164a, 164b, 164c, and 164d). The plaque scoring element can also be made from a flexible strip, wire, cord, or rod, such as one made from a biocompatible metal or polymeric material, and can be the same material that is used to make the portion of the elongate member that resides within the channel. The plaque scoring elements may have a "loop" shape. As shown in FIG. 8, the plaque scoring elements have piriform (e.g., pear or teardrop) shaped curves with tapered ends, and an opening defined by the shape of the element. However, the plaque scoring elements can have different shapes or configurations, such as the oval and rectangular shapes as shown in FIGS. 9a and 9b, respectively. The scoring element may also have, asymmetric, braided, triangular, and trapezoidal shapes. In some configurations, the openings within the shapes defined by the scoring elements can be partially or fully filled by structural features, such as additional wire portions (167, 169) that are arranged across the opening, such as illustrated in FIGS. 9c and 9d. The additional features may provide the scoring element with a "grid" or "grate" pattern. The plaque scoring elements may have dimensions (width and/or height) of up to about 4 mm, up to about 3 mm, up to about 2 mm, or up to about 1 mm.

Figure 10:
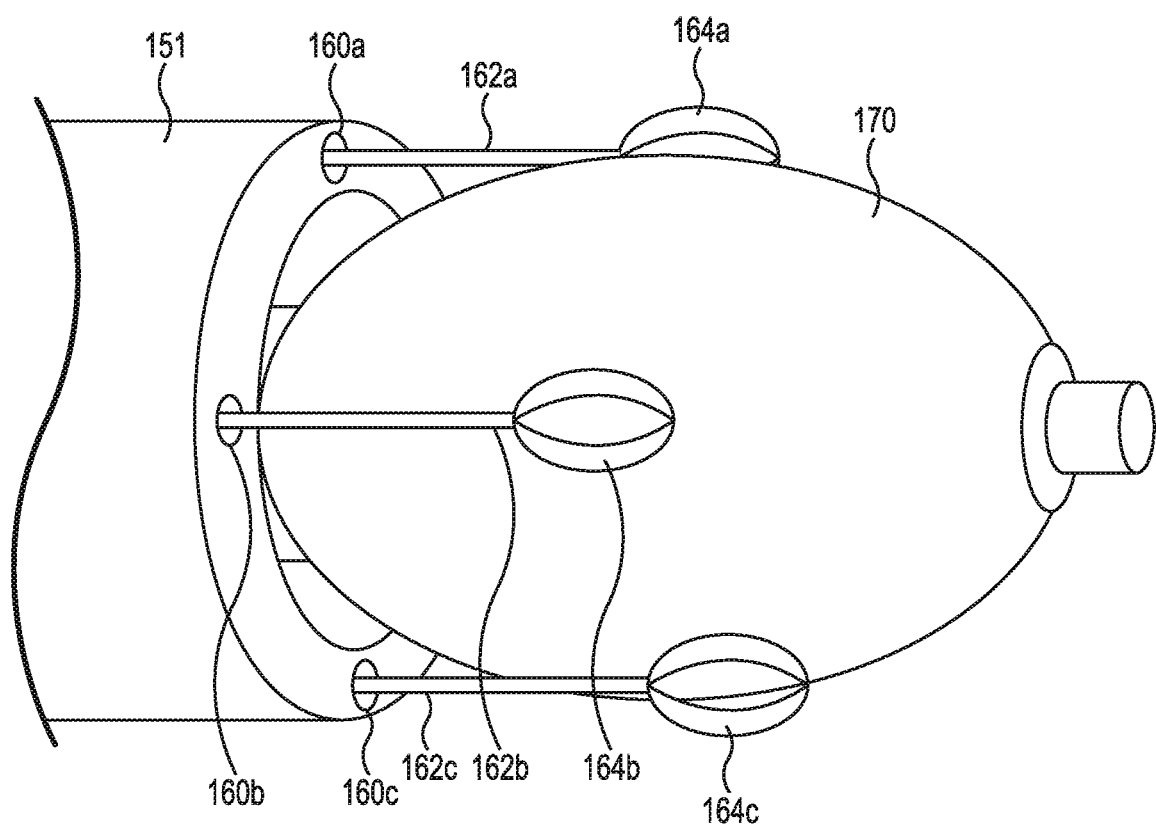
FIG. 10 is a perspective view of the distal end of a plaque treatment system with plaque scoring members being forced in an outwards direction by an expanded balloon.

In some modes of practice, treatment of a plaque-containing portion of an artery can be performed by forcing one or more of the plaque scoring elements against an arterial plaque. Reference is made to FIG. 10, which shows a balloon portion 170 of a balloon catheter, which has been moved distally out of the inner diameter of the distal end of the catheter tube 151. The elongate members with plaque treatment elements (164a, 164b, and 164c are shown), can also be moved distally in order to provide them at a desired location for treating a plaque. In some modes of practice the plaque to be treated may dictate that one of the scoring element should be moved distally and positioned proximate to the plaque, whereas in other modes of practice two or more scoring elements may be moved distally and positioned proximate to the plaque. Further, two or more scoring elements may be extended different lengths. After the scoring elements have been positioned as desired, the balloon can be inflated to force the scoring element(s) up against the plaque so the plaque can be abraded. Further, when the scoring element(s) are in contact with the plaque they can be moved, such as in proximal and distal directions, by a user controlling movement of the associated wires at the proximal end.

Figure 11:
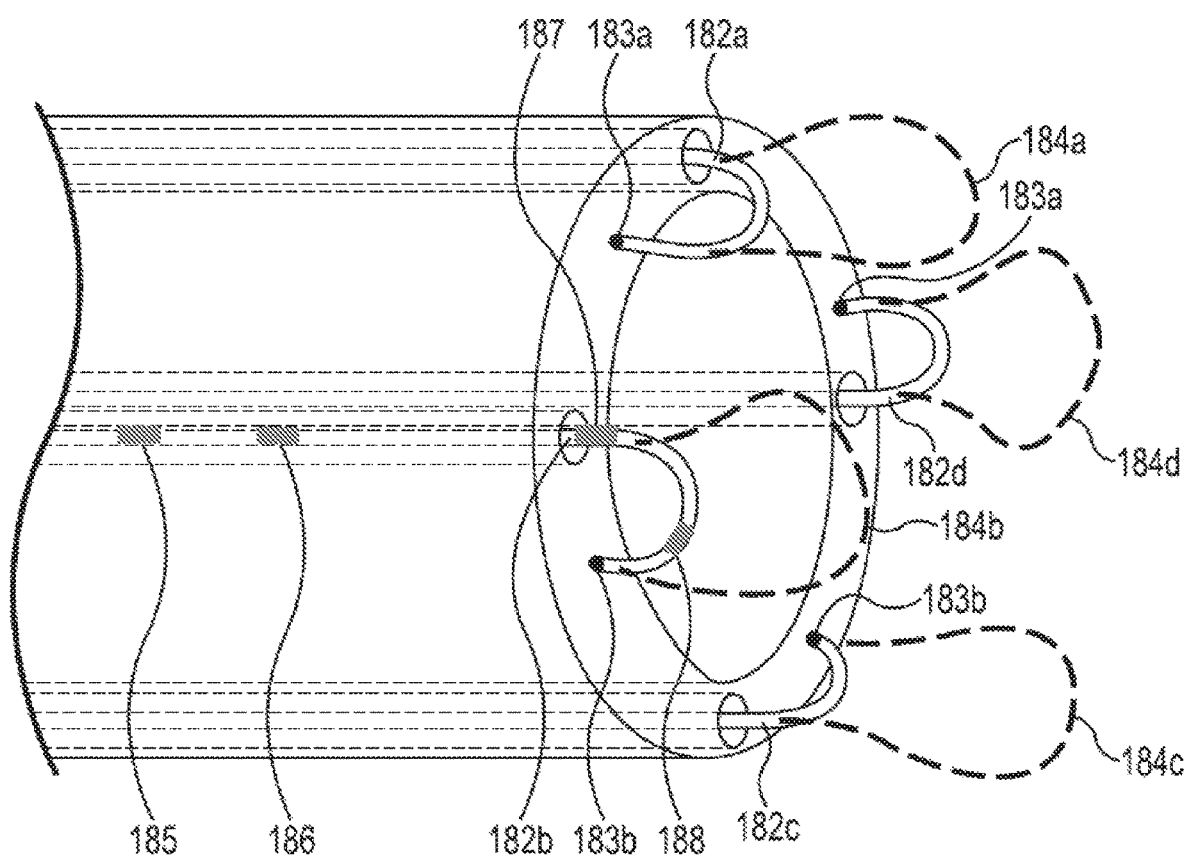
FIG. 11 is a perspective view of the distal end of another embodiment of a plaque treatment system with plaque scoring members.

In another embodiment of the catheter assembly as shown in FIG. 11, elongate members (182a, 182b, 182c, and 182d) are formed of a flexible wire, cord, or rod, such as one made from a biocompatible metal or polymeric material, with their distal ends (183a, 183b, 183c, and 183d) fixed to a portion of the distal end of the catheter tube. The elongate members can be advanced distally which causes extension of additional lengths of the wires from apertures, and formation of larger "loops" (dashed lines 184a, 184b, 184c, and 184d) which can function as plaque scoring elements. Similar to the mode of practice described with reference to FIG. 10, after these larger loops are formed and positioned proximal to a plaque as desired, the balloon can be inflated to force the loops (scoring element(s)) up against the plaque so the plaque can be abraded. Further, the elongate members can be moved when in contact with the plaque they can be moved so the size of the loops are changed, wherein movement can be controlled by a user at the proximal end.

Optionally, the elongate members can include an imaging material (paramagnetic material, a radioisotope, and non-toxic radio-opaque material) at one or more locations along the length of the member, to facilitate the location of one of more parts of the member during a procedure. FIG. 11 shows imaging markers at locations 185-188 along the length of elongate member 182b.

Figure 12:
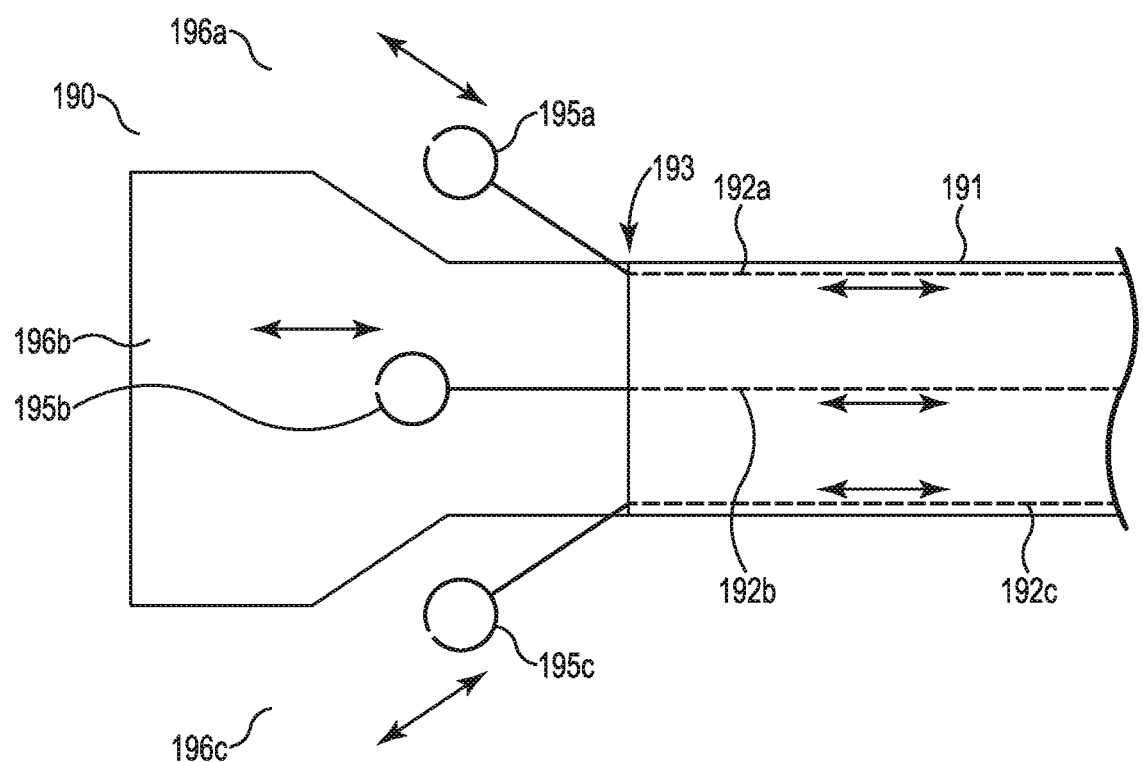
FIG. 12 is an illustration of the proximal end of an embodiment of a plaque treatment system.

In some modes of practice, the control of movement of the elongate members with scoring elements can be explained with reference to FIG. 12, which illustrates the proximal end 190 of an exemplary embodiment of the catheter assembly. The wires of elongate members (192a, 192b, and 192c) are within the wall of catheter tube 191, exit the wall at location 193, and then continue to their proximal ends (195a, 195b, and 195c), which can include a feature that facilitates control over the proximal and distal movement of the member. For example, the feature can be a circular member sized to allow insertion of a finger of a user. In this manner, the movement of multiple elongate members can be controlled by the finger of one hand of the user. FIG. 11 also shows retracted positions (196a, 196b, and 196c) and advanced positions (195a, 195b, and 195c) of the elongate members, which affect the positioning of the plaque scoring members (FIG. 8, 10), or the length of the loops (FIG. 11).

In another embodiment, the disclosure provides a plaque treatment or clot removal catheter assembly having a catheter tube with proximal and distal catheter ends and inner and outer surfaces defining a catheter wall and an inner diameter of the catheter tube, with the catheter tube configured for insertion within the vasculature. In the catheter tube there are one or more channel(s) within the catheter wall that are parallel to an axis of the catheter tube, with the channel(s) extending from the proximal to distal end of the catheter tube. The assembly also includes multiple elongate members each having a distal portion comprising a plaque treatment or clot removal member having the shape of a spade/blade. For example, the blade/spade has a curved surface, two non-parallel edges that taper to a distal point defining the distal end of the spade/blade member, and at least one distal edge meeting the two non-parallel edges. The curvature of the curved surface can be the same or about the same as the curvature of the catheter tube. The elongate members can be moved distally so the tips and edges of the plaque treatment or clot removal member having the shape of a blade/spade are brought towards each other.

What is claimed is:

1. A plaque treatment catheter assembly comprising:
a catheter tube comprising:
proximal and distal catheter ends;
an inner and outer diameter defining a catheter wall, the inner diameter defining a lumen of the catheter tube, the catheter tube capable of being inserted within a vasculature;
one or more channel(s) within the catheter wall and between the inner and outer diameters of the catheter wall and that are parallel to an axis of the catheter tube and that extend from the proximal to distal end of the catheter tube; and
one or more elongate member(s) having a distal portion comprising a plaque scoring member or a clot retrieval member, and having a portion proximal to the distal portion configured to move within the one or more channel(s); and
an expandable member that is movable within and out of the lumen of the catheter tube that can be expanded to cause movement of the one or more plaque scoring member(s) or the one or more clot retrieval member(s).

2. The plaque treatment catheter assembly of claim 1 comprising 2-6 channel(s) within the catheter wall that are spaced from one another in the catheter wall.

3. The plaque treatment catheter assembly of claim 1, wherein the one or more elongate member(s) is in the form of a flexible wire, a flexible cord, or a flexible rod.

4. The plaque treatment catheter assembly of claim 3, wherein the flexible wire, cord, or rod is made of a biocompatible metal or polymeric material.

5. The plaque treatment catheter assembly of claim 3, wherein the flexible wire, cord, or rod has a diameter in the range of 0.05 mm to 0.5 mm, and the one or more channel(s) has a diameter that is greater than the diameter of the flexible wire, cord, or rod.

6. The plaque treatment catheter assembly of claim 3, wherein the flexible wire, cord, or rod has a distal end that is fixed to a portion of the distal end of the catheter tube, and the plaque scoring member or the clot retrieval member formed from the flexible wire, cord, or rod is distal to the distal end of the catheter tube.

7. The plaque treatment catheter assembly of claim 1, wherein the plaque scoring member or the clot retrieval member is configured to form a loop when the one or more elongate member(s) is extended distally from the one or more channel(s).

8. The plaque treatment catheter assembly of claim 7, wherein the loop is configured to be positioned proximal to a plaque, and the expandable member is inflated to force the loop against the plaque.

9. The plaque treatment catheter assembly of claim 1, wherein movement of the one or more elongate member(s) is controlled at the proximal end of the catheter tube.

\* \* \* \* \*